(12) United States Patent
Sakai et al.

(10) Patent No.: US 8,597,424 B2
(45) Date of Patent: Dec. 3, 2013

(54) COMPOSITION AND METHOD FOR FORMING AN ALUMINUM FILM (75) Inventors: Tatsuya Sakai, Chuo-ku (JP); Yasuo Matsuki, Chuo-ku (JP); Tetsuo Tominaga, Chuo-ku (JP)

(73) Assignee: JSR Corporation, Tokyo (JP)

( * ) Notice: Subject to any disclaimer, the term of this patent is extended or adjusted under 35 U.S.C. 154(b) by 701 days.

(21) Appl. No.: 12/808,843

(22) PCT Filed: Dec. 24, 2008

(86) PCT No.: PCT/JP2008/073917
§ 371 (c)(1),
(2), (4) Date: Jun. 17, 2010

(87) PCT Pub. No.: WO2009/082031
PCT Pub. Date: Jul. 2, 2009

(65) Prior Publication Data
US 2011/0229654 A1    Sep. 22, 2011

(30) Foreign Application Priority Data

Dec. 26, 2007   (JP) ................................ 2007-334242

(51) Int. Cl.
| C09D 185/00 | (2006.01) |
| B32B 15/20 | (2006.01) |
| C09D 5/00 | (2006.01) |
| C07C 211/65 | (2006.01) |
| C07F 5/06 | (2006.01) |

(52) U.S. Cl.
CPC .............. *C09D 185/00* (2013.01); *B32B 15/20* (2013.01); *C09D 5/00* (2013.01); *C07C 211/65* (2013.01); *C07F 5/069* (2013.01)
USPC ..................... 106/287.17; 427/553; 427/97.4; 427/98.4; 427/229

(58) Field of Classification Search
USPC ............ 106/287.17; 427/553, 97.4, 98.4, 229
See application file for complete search history.

(56) References Cited

U.S. PATENT DOCUMENTS

| 4,006,095 A | * | 2/1977 | Hoffman et al. .............. 423/266 |
| 4,748,260 A | | 5/1988 | Marlett |
| 5,191,099 A | | 3/1993 | Gladfelter et al. |
| 6,121,443 A | | 9/2000 | Shin |

FOREIGN PATENT DOCUMENTS

| JP | 63-190890 | 8/1988 |
| JP | 2000-86673 | 3/2000 |
| JP | 2002-338891 | 11/2002 |
| JP | 2005-206925 | 8/2005 |

(Continued)

OTHER PUBLICATIONS

Frasier et al., "Aluminum hydride adducts of trimethylamine: vibrational spectra and structure" JACS, 1963, 698, 3742-3749.*

(Continued)

*Primary Examiner* — David M Brunsman
(74) *Attorney, Agent, or Firm* — Oblon, Spivak, McClelland, Maier & Neustadt, L.L.P.

(57) ABSTRACT

A composition for forming an aluminum film, comprising a complex represented by the following formula (1) and a complex represented by the following formula (2), the molar ratio of the complex represented by the following formula (1) and the complex represented by the following formula (2) being 40:60 to 85:15:

$$AlH_3 \cdot NR^1R^2R^3 \qquad (1)$$

$$AlH_3 \cdot (NR^1R^2R^3)_2 \qquad (2)$$

(in the above formulas (1) and (2), $R^1$, $R^2$ and $R^3$ are each independently a hydrogen atom, alkyl group, cycloalkyl group, alkenyl group, alkynyl group, aryl group or aralkyl group.).

10 Claims, 3 Drawing Sheets

(56) References Cited

FOREIGN PATENT DOCUMENTS

| JP | 2006-213943 | 8/2006 |
| JP | 2006-237392 | 9/2006 |
| JP | 2007-287821 | 11/2007 |

OTHER PUBLICATIONS

Kazuo Maeda, "Semiconductor Process for Beginners", Kogyo Chosakai Publishing, Inc., (2000), pp. 232-239 (with partial english translation).

John K. Ruff, et al., "The Amine Complexes of Aluminum Hydride", The Journal of the American Chemical Society, vol. 82, 1960, pp. 2141-2144.

G. W. Fraser, et al,. "Aluminium Hydride Adducts of Trimerhylamine: Vibrational Spectra and Structure", Journal of Chemical Society, vol. 113, Jul. 1963, pp. 3742-3749.

Jerry L. Atwood, et al., "Tertiary Amine Stabilized Dialane", Journal of the American Chemical Society, vol. 113, No. 2, Oct. 9, 1991, pp. 8183-8185.

Egon Wiberg, et al., "A monomer and a dimmer form of aluminum hydride, AlI-3", Zeitschrt fuer Naturforschung, 1952, 7b, p. 578-579 (abstract).

* cited by examiner

COMPOSITION AND METHOD FOR FORMING AN ALUMINUM FILM

This application is a 371 of PCT/JP08/73917 filed Dec. 24, 2008. Priority to Japanese patent application No. 2007-334242, filed Dec. 26, 2007, is claimed.

TECHNICAL FIELD

The present invention relates to a composition for forming an aluminum film and a method of forming an aluminum film. More specifically, it relates to a coating composition for forming an aluminum film, which has excellent storage stability, and a method of forming an aluminum film easily at a low cost by a coating technique using the composition.

BACKGROUND ART

A metal aluminum material is widely used in the electrode wiring of a semiconductor device typified by DRAM and the reflection film of an optical device since it has high conductivity and high optical properties. An aluminum film has been formed mainly by sputtering, deposition or chemical vapor deposition (refer to JP-A 2000-86673 and "Semiconductor Process for Beginners" written by Kazuo Maeda and published by Kogyo Chosakai Publishing, Inc., pp. 232-239). However, as these processes require expensive and large equipment such as a vacuum chamber and a high-voltage current apparatus, they are costly and it is difficult to apply them to large-sized substrates, which is industrially disadvantageous. Further, semiconductor devices are becoming finer in pattern or optical devices are becoming more complicated in shape. When an aluminum film is formed in a semiconductor device having a fine pattern or an optical device having a complicated shape by a conventionally known technique, a defect may be produced in the formed aluminum film, or step coverage may become short.

Meanwhile, methods of forming an aluminum film from a coating composition which comprises an aluminum compound or a complex of an amine complex and aluminum hydride have recently been proposed (refer to JP-A 2002-338891 and JP-A 2006-237392). Since these technologies do not require expensive equipment, they have a low film forming cost and a satisfactory step coverage even for a substrate having a trench with a high aspect ratio. However, as these compositions are unsatisfactory in terms of long-term storage stability in some cases, further improvement has been desired.

DISCLOSURE OF THE INVENTION

It is an object of the present invention which has been made in view of the above situation to provide a coating composition for forming an aluminum film, which has excellent long-term storage stability and a method of forming an aluminum film easily at a low coat by applying the composition.

According to the present invention, firstly, the above object is attained by a composition for forming an aluminum film, comprising a complex represented by the following formula (1) and a complex represented by the following formula (2), the molar ratio of the complex represented by the following formula (1) and the complex represented by the following formula (2) being 40:60 to 85:15:

(1)

(2)

(in the above formulas (1) and (2), $R^1$, $R^2$ and $R^3$ are each independently a hydrogen atom, alkyl group, cycloalkyl group, alkenyl group, alkynyl group, aryl group or aralkyl group.).

Preferably, the above composition for forming an aluminum film further comprises a titanium compound.

Secondly, the above object of the present invention is attained by a method of forming an aluminum film, comprising the steps of:

applying the above composition for forming an aluminum film to a substrate to form a coating film; and subjecting the coating film to at least one of a heat treatment and an photoirradiation treatment.

Thirdly, the above object of the present invention is attained by a method of producing the above composition for forming an aluminum film, comprising the steps of:

synthesizing the complex represented by the above formula (1) by reacting lithium aluminum hydride with a hydrohalogenic acid salt of $NR^1R^2R^3$ ($R^1$, $R^2$ and $R^3$ areas defined in the above formulas (1) and (2)) in an ether solvent at a temperature of 0° C. or lower;

synthesizing the complex represented by the above formula (2) by reacting lithium aluminum hydride with a hydrohalogenic acid salt of $NR^1R^2R^3$ ($R^1$, $R^2$ and $R^3$ areas defined in the above formulas (1) and (2)) in a hydrocarbon solvent at a temperature higher than 30° C.; and mixing these complexes together.

In the fourth place, the above object of the present invention is attained by a method of producing the above composition for forming an aluminum film, comprising the step of:

synthesizing a complex mixture of the complex represented by the above formula (1) and the complex represented by the above formula (2) in a molar ratio of 40:60 to 85:15 in a batch manner by reacting lithium aluminum hydride with a hydrohalogenic acid salt of $NR^1R^2R^3$ ($R^1$, $R^2$ and $R^3$ are as defined in the above formulas (1) and (2)) in an ether solvent at 5 to 20° C. or a hydrocarbon solvent at 25 to 30° C.

The term "compound" as used herein denotes a concept comprehending a complex compound when it contains a metal atom.

BEST MODE FOR CARRYING OUT THE INVENTION

The complex represented by the above formula (1) and the complex represented by the above formula (2) are each a complex of a compound represented by the following formula (3) and aluminum hydride.

(in the above formula (3), $R^1$, $R^2$ and $R^3$ are as defined in the above formulas (1) and (2).)

The aluminum hydride contained in these complexes (commonly called "alan") is a compound consisting of aluminum and hydrogen atoms and generally represented by $AlH_3$.

The alkyl group represented by $R^1$, $R^2$ and $R^3$ in the above formulas (1) and (2) is preferably an alkyl group having 1 to 12 carbon atoms, such as methyl group, ethyl group, propyl group, cyclopropyl group, butyl group, pentyl group, hexyl group, heptyl group, octyl group, nonyl group, decyl group, undecyl group, dodecyl group, 2-methylbutyl group or 2-ethylhexyl group.

The cycloalkyl group represented by $R^1$, $R^2$ and $R^3$ is preferably a cycloalkyl group having 3 to 12 carbon atoms such as cyclohexyl group.

The alkenyl group represented by $R^1$, $R^2$ and $R^3$ is preferably an alkenyl group having 2 to 10 carbon atoms such as vinyl group, allyl group or crotyl group.

The alkynyl group represented by $R^1$, $R^2$ and $R^3$ is preferably an alkynyl group having 2 to 10 carbon atoms such as ethynyl group or phenylethynyl group.

The aryl group represented by $R^1$, $R^2$ and $R^3$ is preferably an aryl group having 6 to 12 carbon atoms such as phenyl group.

The aralkyl group represented by $R^1$, $R^2$ and $R^3$ is preferably an aralkyl group having 7 to 13 carbon atoms such as benzyl group.

Illustrative examples of the compound represented by the above formula (3) include ammonia, trimethylamine, triethylamine, dimethylethylamine, methyldiethylamine, tri-n-propylamine, tri-isopropylamine, tricyclopropylamine, tri-n-butylamine, triisobutylamine, tri-t-butylamine, tri-2-methylbutylamine, tri-n-hexylamine, tricyclohexylamine, tri (2-ethylhexyl)amine, trioctylamine, triphenylamine, tribenzylamine, dimethylphenylamine, diethylphenylamine, diisobutylphenylamine, methyldiphenylamine, ethyldiphenylamine, isobutyldiphenylamine, dimethylamine, diethylamine, di-n-propylamine, diisopropylamine, dicyclopropylamine, di-n-butylamine, diisobutylamine, di-t-butylamine, methylethylamine, methylbutylamine, di-n-hexylamine, dicyclohexylamine, di(2-ethylhexyl)amine, dioctylamine, diphenylamine, dibenzylamine, methylphenylamine, ethylphenylamine, isobutylphenylamine, methylallylamine, methylvinylamine, methyl(phenylethynyl)amine, phenyl (phenylethynyl)amine, methylamine, ethylamine, n-propylamine, isopropylamine, cyclopropylamine, n-butylamine, isobutylamine, t-butylamine, 2-methylbutylamine, n-hexylamine, cyclohexylamine, 2-ethylhexylamine, octylamine, phenylamine and benzylamine.

The molar ratio of the complex represented by the above formula (1) and the complex represented by the above formula (2) contained in the composition for forming an aluminum film of the present invention, that is, the ratio (M(1):M (2)) of the number of moles M(1) of the complex represented by the above formula (1) and the number of moles M (2) of the complex represented by the above formula (2) is 40:60 to 85:15, preferably 50:50 to 85:15, more preferably 70:30 to 85:15.

The molar ratio of the complex represented by the above formula (1) and the complex represented by the above formula (2) can be calculated from the ratio of the peak area of a peak attributed to the hydrogen atoms contained in aluminum hydride and the peak area of a peak attributed to the compound represented by the above formula (3) in $^1$H-NMR.

The complex represented by the above formula (1) and the complex represented by the above formula (2) contained in the composition for forming an aluminum film of the present invention can be synthesized in accordance with the methods described in J. K. Ruff et al., J. Amer. Chem. Soc., vol. 82, p. 2141, 1960, G. W. Fraser et al, J. Chem. Soc., p. 3742, 1963, and J. L. Atwood et al., J. Amer. Chem. Soc., vol. 113, p. 8133, 1991. For example, they can be synthesized by reacting lithium aluminum hydride with a hydrohalogenic acid salt of a compound represented by the above formula (3). Examples of the halogen atom of the above hydrohalogenic acid salt include chlorine atom, bromine atom and iodine atom, out of which the chlorine atom is preferred.

The inventors of the present invention have found that when lithium aluminum hydride is reacted with a hydrohalogenic acid salt of a compound represented by the above formula (3), the formation ratio of the complex represented by the above formula (1) and the complex represented by the above formula (2) depends on reaction conditions adopted. They have further found that the complex represented by the above formula (1) and the complex represented by the above formula (2) can be thereby obtained in any mixing ratio and that a composition for forming an aluminum film having specifically excellent storage stability can be obtained when the mixing ratio (molar ratio) of these complexes is set to the above specific range. The present invention has been accomplished based on this finding.

To set the molar ratio of the complex represented by the above formula (1) and the complex represented by the above formula (2) to the above range, the following methods are preferably employed.

<method A> The complex represented by the above formula (1) and the complex represented by the above formula (2) are synthesized independently and mixed together.

<method B> A mixture of the complex represented by the above formula (1) and the complex represented by the above formula (2) in a molar ratio of 40:60 to 85:15 is synthesized in a batch manner.

The above method A and the above method B will be described in detail hereinunder.

<Method A>

—Method of Synthesizing the Complex Represented by the Above Formula (1)—

The complex represented by the above formula (1) can be obtained by reacting lithium aluminum hydride with a hydrohalogenic acid salt, preferably a hydrochloric acid salt of a compound represented by the above formula (3) in an ether solvent at 0° C. or lower, As for the ratio of lithium aluminum hydride and the hydrohalogenic acid salt of the compound represented by the above formula (3) used in the reaction, the amount of the hydrohalogenic acid salt of the compound represented by the above formula (3) is preferably 1.0 to 3.5 moles, more preferably 1.1 to 2.2 moles based on 1 mole of lithium aluminum hydride.

Examples of the above ether solvent include diethyl ether, dipropyl ether, dibutyl ether, ethylene glycol dimethyl ether, ethylene glycol diethyl ether, ethylene glycol methyl ethyl ether, diethylene glycol dimethyl ether, diethylene glycol diethyl ether, diethylene glycol methyl ethyl ether, tetrahydrofuran, tetrahydropyran, bis(2-methoxyethyl)ether, p-dioxane, anisole, 2-methylanisole, 3-methylanisole, 4-methylanisole, phentol, 2-methylphentol, 3-methylphentol, 4-methylphentol, veratrol, 2-ethoxyanisole and 1,4-dimethoxybenzene.

The amount of the solvent is preferably set to ensure that the total weight of all the components except for the solvent in the reaction solution becomes 5 to 70 wt % based on the total weight of the solution.

The reaction temperature can be 0° C. or lower but preferably −60 to 0° C., more preferably −30 to −5° C. The reaction time is preferably 1 to 6 hours, more preferably 1 to 3 hours.

The complex represented by the above formula (1) can be obtained by the above method in an amount of not less than 90 mole %, specifically not less than 95 mole % based on the total of the complex represented by the above formula (1) and the complex represented by the above formula (2).

The complex represented by the above formula (1) obtained as described above may be used for the preparation of the composition for forming an aluminum film of the present invention as a reaction solution directly or after this is isolated and purified. The isolation of the complex represented by the above formula (1) can be carried out by removing the solvent after an undissolved matter such as a by-product is removed from the reaction solution. As means of purifying the complex represented by the above formula (1), column chromatography, distillation, re-crystallization and extraction may be employed.

—Method of Synthesizing the Complex Represented by the Above Formula (2)—

The complex represented by the above formula (2) can be preferentially obtained by reacting lithium aluminum hydride with a hydrohalogenic acid salt, preferably a hydrochloric acid salt of a compound represented by the above formula (3) in a hydrocarbon solvent at a temperature higher than 30° C.

As for the ratio of lithium aluminum hydride and the hydrohalogenic acid salt of the compound represented by the above formula (3) used in the reaction, the amount of the hydrohalogenic acid salt of the compound represented by the above formula (3) is preferably 2.0 to 7.0 moles, more preferably 2.2 to 4.4 moles based on 1 mole of lithium aluminum hydride.

The above hydrocarbon solvent is selected from an aliphatic hydrocarbon and an aromatic hydrocarbon. Examples of the above aliphatic hydrocarbon include n-pentane, cyclopentane, n-hexane, cyclohexane, n-heptane, cycloheptane and n-octane; and examples of the above aromatic hydrocarbon include benzene, toluene and xylene.

The amount of the solvent is preferably set to ensure that the total weight of all the components except for the solvent in the reaction solution becomes 5 to 70 wt % based on the total weight of the solution.

The reaction temperature can be higher than 30° C. but preferably 32 to 50° C., more preferably 35 to 40° C. The reaction time is preferably 0.5 to 4 hours, more preferably 1 to 2.5 hours.

The complex represented by the above formula (2) can be preferentially obtained as described above.

The complex represented by the above formula (2) obtained as described above may be directly used for the preparation of the composition for forming an aluminum film of the present invention as a reaction solution but preferably after it is purified. As means of purification, column chromatography, distillation, recrystallization and extraction may be employed. Out of these, purification by distillation is preferred because a high-purity complex is obtained. As for distillation conditions, the complex is preferably distilled at a temperature of −10 to 80° C. and a pressure of 10 to 3,000 Pa, more preferably at a temperature of 0 to 50° C. and a pressure of 50 to 1,500 Pa.

In the method A, the complex represented by the above formula (1) and the complex represented by the above formula (2) obtained as described above are preferably dissolved in a solvent together with optional additives which are used as required and will be described hereinafter to obtain the composition for forming an aluminum film of the present invention.

<Method B>

In the method B, a mixture of the complex represented by the above formula (1) and the complex represented by the above formula (2) in the above preferred mixing ratio (molar ratio) is synthesized in a batch manner.

This can be realized by carrying a reaction between lithium aluminum hydride and a hydrohalogenic acid salt, preferably a hydrochloric acid salt of a compound represented by the above formula (3) in an ether solvent at 5 to 20° C. or in a hydrocarbon solvent at 25 to 30° C.

When the reaction is carried out in an ether solvent, examples of the ether solvent are the same as those enumerated above which may be used to synthesize the complex represented by the above formula (1) in the method A. The amount of the solvent is preferably set to ensure that the total weight of all the components except for the solvent in the reaction solution becomes 5 to 70 wt % based on the total weight of the solution. The reaction temperature is preferably 5 to 20° C. The reaction time is preferably 0.5 to 6 hours, more preferably 1 to 3 hours.

When the reaction is carried out in a hydrocarbon solvent, examples of the hydrocarbon solvent are the same as those enumerated above which may be used to synthesize the complex represented by the above formula (2) in the method A. The amount of the solvent is preferably set to ensure that the total weight of all the components except for the solvent in the reaction solution becomes 5 to 70 wt % based on the total weight of the solution. The reaction temperature is preferably 25 to 30° C. The reaction time is preferably 0.3 to 4 hours, more preferably 1 to 3 hours.

In the method B, a mixture of the complex represented by the above formula (1) and the complex represented by the above formula (2) can be synthesized in any mixing ratio in a batch manner by suitably selecting the solvent and the reaction temperature from the above range. For example, as the polarity of the solvent used is made higher or the reaction temperature is made lower, the amount of the formed complex represented by the above formula (1) can be increased. On the other hand, as the polarity of the solvent is made lower or the reaction temperature is made higher, the amount of the formed complex represented by the above formula (2) can be increased.

In the method B, a mixture of the complex represented by the above formula (1) and the complex represented by the above formula (2) synthesized in a batch manner as described above is preferably dissolved in a solvent together with optional additives which are used as required and will be described hereinafter to obtain the composition for forming an aluminum film of the present invention.

<Optional Additives>

The composition for forming an aluminum film of the present invention which contains the complex represented by the above formula (1) and the complex represented by the above formula (2) in the above mixing ratio may contain optional additives as required. The additives include a titanium compound.

Examples of the titanium compound include compounds represented by the following formulas (4) to (8).

$$Ti(OR^4)_4 \quad (4)$$

(in the formula (4), $R^4$ is an alkyl group or alkyl halide group having 1 to 10 carbon atoms, cycloalkyl group having 3 to 12 carbon atoms, phenyl group or phenyl halide group.)

$$Ti(OR^5)_xL_{4-x} \quad (5)$$

(in the formula (5), $R^5$ is an alkyl group or alkyl halide group having 1 to 10 carbon atoms, cycloalkyl group having 3 to 12 carbon atoms, phenyl group or phenyl halide group, and L is a group represented by the following formula:

($R^6$ and $R^7$ are the same or different and each an alkyl group or alkyl halide group having 1 to 10 carbon atoms, alkoxyl group having 1 to 10 carbon atoms, phenyl group, phenyl halide group, phenoxy group or alkylphenoxy group having an alkyl group with 1 to 10 carbon atoms) and x is an integer of 0 to 3.)

$$Ti(OR^8)_y(X)_{4-y} \qquad (6)$$

(in the formula (6), $R^8$ is an alkyl group having 1 to 10 carbon atoms or phenyl group, X is a halogen atom, and y is an integer of 0 to 3.)

$$Ti(NR^9)_4 \qquad (7)$$

(in the formula (7), $R^9$ is an alkyl group having 1 to 10 carbon atoms, alkoxyl group having 1 to 10 carbon atoms or phenyl group.)

$$Ti(Cp)_n(Y)_{4-n} \qquad (8)$$

(in the formula (8), Cp is a cyclopentadienyl group, and Y is a halogen atom, alkyl group having 1 to 10 carbon atoms or phenyl group, and n is an integer of 1 to 4, with the proviso that when there are more than one Y, they may be the same or different.)

$R^4$ in the above formula (4) and $R^5$ in the above formula (5) are each preferably a methyl group, ethyl group, n-propyl group, i-propyl group, n-butyl group, t-butyl group, cyclohexyl group or trifluoromethyl group, more preferably a methyl group, ethyl group, n-propyl group, i-propyl group, n-butyl group, t-butyl group, hexyl group, cyclohexyl group or phenyl group.

$R^6$ and $R^7$ of L in the above formula (5) are each preferably a methyl group, ethyl group, n-propyl group, i-propyl group, n-butyl group, t-butyl group, methoxyl group, ethoxyl group, n-propoxyl group, i-propoxyl group, n-butoxyl group, t-butoxyl group, phenoxyl group, methylphenoxyl group or trifluoromethyl group, more preferably a methyl group, ethyl group, i-propyl group, t-butyl group, methoxyl group, ethoxyl group, i-propoxyl group, t-butoxyl group or trifluoromethyl group.

Examples of the compound represented by the above formula (4) include titanium methoxide, titanium ethoxide, titanium-n-propoxide, titanium-n-nonyl oxide, titanium stearyl oxide, titanium isopropoxide, titanium-n-butoxide, titanium isobutoxide, titanium-t-butoxide, titanium trimethylsiloxide, titanium-2-ethylhexoxide, titanium methoxypropoxide, titanium phenoxide, titanium methylphenoxide, titanium fluoromethoxide and titanium chlorophenoxide.

Examples of the titanium compound represented by the above formula (5) include tetrakis(penta-2,4-diketo)titanium, tetrakis(2,2,6,6-tetramethylhepta-3,5-diketo)titanium, tetrakis(1-ethoxybutane-1,3-diketo)titanium, tetrakis(1,1,1,5,5,5-hexafluoropenta-2,4-diketo)titanium, (2,2-dimethylhexa-3,5-diketo)titanium, bis(penta-2,4-diketo)titanium dimethoxide, bis(2,2,6,6-tetramethylhepta-3,5-diketo)titanium dimethoxide, bis(1-ethoxybutane-1,3-diketo)titanium dimethoxide, bis(1,1,1,5,5,5-hexafluoropenta-2,4-diketo)titanium dimethoxide, (2,2-dimethylhexa-3,5-diketo)titanium dimethoxide, bis(penta-2,4-diketo)titanium di-i-propoxide, bis(2,2,6,6-tetramethylhepta-3,5-diketo)titanium di-i-propoxide, bis(1-ethoxybutane-1,3-diketo)titanium di-i-propoxide, bis(1,1,1,5,5,5-hexafluoropenta-2,4-diketo)titanium di-i-propoxide and (2,2-dimethylhexa-3,5-diketo)titanium di-i-propoxide.

$R^8$ in the above formula (6) is preferably a methyl group, ethyl group, n-propyl group, i-propyl group, n-butyl group or t-butyl group. X is preferably a chlorine atom.

Examples of the compound represented by the above formula (6) include trimethoxytitanium chloride, triethoxytitanium chloride, tri-n-propoxytitanium chloride, tri-i-propoxytitanium chloride, tri-n-butoxytitanium chloride, tri-t-butoxytitanium chloride, triisostearoyltitanium chloride, dimethoxytitanium dichloride, diethoxytitanium dichloride, di-n-propoxytitanium dichloride, di-i-propoxytitanium dichloride, di-n-butoxytitanium dichloride, di-t-butoxytitanium dichloride, diisostearoyltitanium dichloride, methoxytitanium trichloride, ethoxytitanium trichloride, n-propoxytitanium trichloride, i-propoxytitanium trichloride, n-butoxytitanium trichloride, t-butoxytitanium trichloride, isostearoyltitanium trichloride and titanium tetrachloride.

$R^9$ in the above formula (7) is preferably a methyl group, ethyl group, i-propyl group, t-butyl group, i-propoxyl group, t-butoxyl group or phenyl group.

Examples of the compound represented by the above formula (7) include tetrakis(dimethylamino)titanium, tetrakis(diethylamino)titanium, tetrakis(di-t-butoxyamino)titanium, tetrakis(di-i-propoxyamino)titanium and tetrakis(diphenylamino)titanium.

Y in the above formula (8) is preferably a chlorine atom, bromine atom, methyl group, ethyl group, t-butyl group or phenyl group.

Examples of the compound represented by the above formula (8) include dicyclopentadienyltitanium dichloride, dicyclopentadienyltitanium dibromide, cyclopentadienyltitanium trichloride, cyclopentadienyltitanium tribromide, dicyclopentadienyldimethyl titanium, dicyclopentadienyldiethyl titanium, dicyclopentadienyldi-t-butyl titanium, dicyclopentadienylphenyl titanium chloride and dicyclopentadienylmethyl titanium chloride.

The content of the titanium compound in the composition for forming an aluminum film of the present invention is preferably not more than 1 mole %, more preferably 0.00001 to 0.1 mole %, much more preferably 0.00005 to 0.01 mole % based on the total of the complex represented by the above formula (1), the complex represented by the above formula (2) and the titanium compound. When the content of the titanium compound falls within the above range, both high embedding property and the stability of the composition can be obtained.

<Composition for Forming an Aluminum Film>

The composition for forming an aluminum film of the present invention comprises the complex represented by the above formula (1) and the complex represented by the above formula (2) in the above mixing ratio (molar ratio) and further optional additives which are used as the case may be and is preferably prepared as a solution composition comprising these components dissolved in a solvent.

The solvent used in the composition for forming an aluminum film of the present invention is not particularly limited if it dissolves the complex represented by the above formula (1), the complex represented by the above formula (2) and optional additives which are used as the case may be and does not react with these. The solvent is selected from a hydrocarbon solvent, an ether solvent and other polar solvents.

Examples of the above hydrocarbon solvent include n-pentane, cyclopentane, n-hexane, cyclohexane, n-heptane, cycloheptane, n-octane, cyclooctane, decane, cyclodecane, dicyclopentadiene hydride, benzene, toluene, xylene, durene, indene, tetrahydronaphthalene, decahydronaphthalene and squalane.

Examples of the above ether solvent include diethyl ether, dipropyl ether, dibutyl ether, ethylene glycol dimethyl ether, ethylene glycol diethyl ether, ethylene glycol methyl ethyl ether, diethylene glycol dimethyl ether, diethylene glycol diethyl ether, diethylene glycol methyl ethyl ether, tetrahydrofuran, tetrahydropyran, bis(2-methoxyethyl)ether, p-dioxane, anisole, 2-methylanisole, 3-methylanisole, 4-methylanisole, phentol, 2-methylphentol, 3-methylphentol, 4-methylphentol, veratrol, 2-ethoxyanisole and 1,4-dimethoxybenzene.

The above polar solvents include methylene chloride and chloroform.

These solvents may be used alone or in combination of two or more.

Out of these, a hydrocarbon solvent or a mixed solvent of a hydrocarbon solvent and an ether solvent is preferred from the viewpoints of solubility and the stability of the obtained composition solution. Out of these, n-pentane, cyclopentane, n-hexane, cyclohexane, n-heptane, cycloheptane, n-octane, benzene, toluene or xylene is preferably used as the hydrocarbon solvent, and diethyl ether, dipropyl ether, dibutyl ether, ethylene glycol diethyl ether, ethylene glycol methyl ethyl ether, tetrahydrofuran, tetrahydropyran, anisole, 2-methylanisole, 3-methylanisole, 4-methylanisole, phentol, veratrol, 2-ethoxyanisole or 1,4-dimethoxybenzene is preferably used as the ether solvent.

The ratio of the total weight of all the components except for the solvent of the composition for forming an aluminum film of the present invention to the total weight of the composition (to be referred to as "solids content" hereinafter) is suitably set according to the thickness of an aluminum film to be formed. For example, when the thickness of the aluminum film is less than 200 nm, the solids content is preferably not less than 5 wt % and less than 55 wt %, more preferably 10 to 50 wt %. When the thickness of the aluminum film is not less than 200 nm, the solids content is preferably 55 to 90 wt %, more preferably 70 to 85 wt %.

The method of producing the composition for forming an aluminum film of the present invention is not particularly limited.

When the above method A is employed to set the mixing ratio of the complex represented by the above formula (1) and the complex represented by the above formula (2) to the above range, a composition obtained by mixing together the complex represented by the above formula (1) and the complex represented by the above formula (2) synthesized in a predetermined ratio in the presence of a solvent and removing an undissolved product such as a by-product may be directly used as the composition for forming an aluminum film. A composition obtained by isolating one of the complex represented by the above formula (1) and the complex represented by the above formula (2) synthesized in the presence of a solvent, mixing it with a reaction solution of the other complex and removing an undissolved product such as a by-product may also be used as the composition for forming an aluminum film. These solutions may be used after the solvent is substituted by a desired solvent as required. Alternatively, a composition may be obtained by isolating both of the synthesized complex represented by the above formula (1) and the synthesized complex represented by the above formula (2) and dissolving them in a desired solvent.

When the method B is employed, a solution obtained by removing an undissolved product such as a by-product from the reaction mixture may be used as the composition for forming an aluminum directly or after the solvent of this solution is substituted by a desired solvent. Alternatively, a composition obtained by re-dissolving a mixture of the complex represented by the above formula (1) and the complex represented by the above formula (2) obtained after the solvent is removed from the reaction mixture in a desired solvent may be used as the composition for forming an aluminum film.

When the composition for forming an aluminum film of the present invention contains a titanium compound, it can be prepared by adding a predetermined amount of the titanium compound solution to a solution containing the complex represented by the above formula (1) and the complex represented by the above formula (2) produced as described above under agitation. The temperature for adding the titanium compound is preferably 0 to 150° C., more preferably 5 to 100° C. The time required for addition is preferably 0.1 to 120 minutes, more preferably 0.2 to 60 minutes. By adding the titanium compound under the above conditions, a stable composition can be obtained.

<Method of Forming an Aluminum Film>

The method of forming an aluminum film of the present invention comprises the steps of applying the composition for forming an aluminum film of the present invention to a substrate so as to form a coating film and subjecting the coating film to at least one of a heat treatment and an photoirradiation treatment to convert the coating film into an aluminum film on the substrate.

The material and shape of the above substrate are not particularly limited. The material of the substrate preferably withstands a heat treatment when the heat treatment is employed in the step of converting the coating film into an aluminum film. The shape of the substrate on which the coating film is to be formed is block-like, plate-like or film-like and not particularly limited, and the surface of the substrate on which the coating film is to be formed may be flat or uneven with a level difference. Examples of the material of the substrate include glasses, metals, plastics and ceramics. The glasses include quartz glass, borosilicate glass, soda glass and lead glass. The metals include gold, silver, copper, nickel, silicon, aluminum, iron and stainless steel. The plastics include polyimide and polyether sulfone.

The substrate to be used in the method of the present invention may have a base film which is formed by applying a solution comprising an organic metal compound containing at least one metal atom selected from the group consisting of titanium, palladium and aluminum and heating it. When the substrate has the above base film, aluminum film formability on the substrate can be further improved.

Examples of the above organic metal compound containing a titanium atom include titanium alkoxides, titanium compounds having an amino group, β-diketone complexes of titanium, titanium compounds having a cyclopentadienyl group and titanium compounds having a halogen atom.

Examples of the above organic metal compound containing a palladium atom include palladium complexes having a halogen atom, acetates of palladium, β-diketone complexes of palladium, complexes of palladium and a compound having a conjugated carbonyl group, and phosphine complexes of palladium.

Examples of the above organic metal compound containing an aluminum atom include aluminum alkoxides, aluminum alkylates and β-diketone complexes of aluminum, excluding complexes of an amine compound and aluminum hydride.

Specific examples of the organic metal compound include the titanium compounds enumerated above which may be contained in the above composition for forming an aluminum film as the organic metal compound containing a titanium atom.

Out of the organic metal compounds containing a palladium atom, the palladium complexes having a halogen atom include allyl palladium chloride, dichlorobis(acetonitrile) palladium and dichlorobis(benzonitrile)palladium; the acetates of palladium include palladium acetate; the β-diketone complexes of palladium include pentane-2,4-dionatopalladium and hexafluoropentane dionatopalladium; the complexes of palladium and a compound having a conjugated carbonyl group include bis(dibenzilideneacetone)palladium; and the phosphine complexes of palladium include bis[1,2-bis(diphenylphosphino)ethane]palladium, bis(triphenylphosphine)palladium chloride, bis(triphenylphosphine) palladium acetate, diacetate bis(triphenylphosphine)palladium, dichloro[1,2-bis(diphenylphosphine)ethane] palladium, trans-dichlorobis(tricyclohexylphosphine) palladium, trans-dichlorobis(triphenylphosphine)palladium, trans-dichlorobis(tri-o-tolylphosphine)palladium and tetrakis(triphenylphosphine)palladium.

Out of the above organic metal compounds containing an aluminum atom, the aluminum alkoxides include aluminum ethoxide, aluminum isopropoxide, aluminum-n-butoxide, aluminum-s-butoxide, aluminum-t-butoxide, aluminum ethoxyethoxyethoxide and aluminum phenoxide; the aluminum alkylates include aluminum acetate, aluminum acrylate, aluminum methacrylate and aluminum cyclohexane butylate; and the β-diketone complexes of aluminum include pentane-2,4-diketoaluminum, hexafluoropentane-2,4-diketoaluminum, 2,2,6,6-tetramethylheptane-3,5-diketoaluminum, bis(ethoxybutane-1,3-diketo)aluminum s-butoxide, (ethoxybutane-1,3-diketo)aluminum di-s-butoxide and (ethoxybutane-1,3-diekto)aluminum diisopropoxide.

Out of these, titanium isopropoxide, aluminum isopropoxide, bis(ethoxybutane-1,3-diketo)titanium diisopropoxide, tetra(pentane-2,4-diketo)titanium, pentane-2,4-diketopalladium, hexafluoropentane-2,4-diketopalladium, pentane-2,4-diketoaluminum or hexafluoropentane-2,4-diketoaluminum is preferably used.

The solvent used in the solution of the organic metal compound containing at least one metal atom selected from the group consisting of titanium, palladium and aluminum is not particularly limited if it can dissolve the organic metal compound. The solvent is selected from an ether, an ester having an ether group, a hydrocarbon, an alcohol, an aprotic polar solvent and a mixture thereof.

Examples of the above ether include tetrahydrofuran, dioxane, ethylene glycol dimethyl ether, ethylene glycol diethyl ether, diethylene glycol dimethyl ether and diethylene glycol diethyl ether; examples of the above ester having an ether group include ethylene glycol monomethyl ether acetate, ethylene glycol monoethyl ether acetate, propylene glycol monomethyl ether acetate, propylene glycol monoethyl ether acetate and 2-acetoxy-1-methoxypropane; examples of the above hydrocarbon include toluene, xylene, hexane, cyclohexane octane, decalin, tetralin and durene; examples of the alcohol include methanol, ethanol and propanol; and examples of the aprotic polar solvent include N-methylpyrrolidone, N,N-dimethylformamide, N,N-dimethylacetamide, hexamethyl phosphoamide and γ-butyrolactone.

The content of the organic metal compound in the solution of the organic metal compound is preferably 0.1 to 10 wt %, more preferably 0.1 to 5 wt %. The solvent from which water and oxygen have been removed is preferably used.

The solution of the organic metal compound is applied to the substrate by a suitable technique such as spin coating, roll coating, curtain coating, dip coating, spray coating or droplet ejection. When the substrate has a trench structure, the width of the opening of the trench is 300 nm or less, and when the aspect ratio of the trench is 5 or more, after the solution of the organic metal compound is applied to the substrate, the substrate is kept at a lower pressure than the ambient pressure during coating for a while, thereby making it possible to apply the organic metal compound to the inside of the trench uniformly. Stated more specifically, the substrate is kept at a pressure (to be referred to as "second pressure" hereinafter) lower than the pressure (to be referred to as "first pressure" hereinafter) at the time of applying the solution of the organic metal compound to the trenched substrate. The second pressure is preferably 1 to 70%, more preferably 10 to 40% of the first pressure. For example, when the pressure at the time of application is $1.01 \times 10^5$ Pa (normal pressure), the second pressure is preferably $1.01 \times 10^3$ to $7.09 \times 10^4$ Pa, more preferably $1.01 \times 10^4$ to $4.05 \times 10^4$ Pa. The time during which the substrate is kept at the second pressure is preferably 10 seconds to 10 minutes, more preferably 10 seconds to 1 minute. After the substrate is kept at the second pressure and then an inert gas is preferably used to return it to the first pressure, the substrate is sent to the subsequent heating step. A series of operations for reducing the pressure, keeping the reduced pressure and returning it to the first pressure may be repeated several times. The time during which the pressure is returned to the first pressure is preferably 3 seconds to 5 minutes, more preferably 5 seconds to 1 minute. The number of repetitions is 10 or less from the viewpoint of film homogeneity and work efficiency, more preferably 5 or less from the viewpoint of work efficiency. The base coating film formed as described above is then heated. The heating temperature is preferably 30 to 350° C., more preferably 40 to 300° C. The heating time is preferably 5 to 90 minutes, more preferably 10 to 60 minutes. The atmosphere during this coating step and the heating step preferably consists of an inert gas such as nitrogen, helium or argon. These steps may be carried out in an atmosphere containing a reducing gas such as hydrogen or an oxidizing gas such as oxygen as required.

The thickness of this base film is preferably 0.001 to 5 μm, more preferably 0.005 to 0.5 μm after heating.

A suitable technique such as spin coating, roll coating, curtain coating, dip coating, spray coating or droplet ejection may be used to apply the above-described composition for forming an aluminum film to the above substrate. Coating conditions which ensure that the composition for forming an aluminum film is spread to every corner of the substrate are adopted according to the shape and size of the substrate. For example, when spin coating is used to apply the composition, the revolution of the spinner may be set to 300 to 2,500 rpm, more specifically 500 to 2,000 rpm. When the substrate has trenches, the ambient pressure may be changed as described above after the solution of the organic metal compound is applied.

To remove a low-boiling point component such as the solvent contained in the composition for forming an aluminum film after the above coating step, a heat treatment may be carried out. As for the heating temperature and time which differ according to the type and boiling point (steam pressure) of the solvent in use, the composition may be heated at 100 to 350° C. for 5 to 90 minutes. At this point, the solvent may be removed at a low temperature while the whole system is placed under reduced pressure. As for the heat treatment conditions under reduced pressure, the composition is preferably heated at 100 to 250° C. for 10 to 60 minutes.

Then, the coating film formed as described above is subjected to at least one of a heat treatment and an photoirradiation treatment so as to convert it into an aluminum film. Thus, the aluminum film is formed on the substrate.

The temperature of the above heat treatment is preferably 60° C. or higher, more preferably 70 to 600° C., much more preferably 100 to 400° C. The heating time is preferably 30 seconds to 120 minutes, more preferably 1 to 90 minutes, much more preferably 10 to 60 minutes.

The light source used for the above photoirradiation treatment is selected from a mercury lamp, deuterium lamp, discharge light of a rare gas, YAG laser, argon laser, carbon dioxide laser and rare gas halogen excimer laser. Examples of the mercury lamp include a low-pressure mercury lamp and a high-pressure mercury lamp. Examples of the rare gas used in the discharge light of the rare gas include argon, krypton and xenon. Examples of the rare gas halogen used in the above rare gas halogen excimer laser include XeF, XeCl, XeBr, KrF, KrCl, ArF and ArCl.

The output of the light source is preferably 10 to 5,000 W, more preferably 100 to 1,000 W. The wavelength of the light source is not particularly limited but preferably 170 to 600 nm. Use of laser light is particularly preferred from the viewpoint of the quality of the formed aluminum film.

The atmosphere in which the above coating step and the heating step/the photoirradiation step are carried out is preferably an inert atmosphere or a reducing atmosphere. The inert atmosphere can be realized by using an inert gas such as nitrogen, helium or argon. The reducing atmosphere can be realized by using a reducing gas such as hydrogen or both of a reducing gas and the above inert gas.

Only one of the above heat treatment and photoirradiation treatment may be carried out, or both of them may be carried out. When both of them are carried out, the order is not limited, and the heat treatment and the photoirradiation treatment may be carried out simultaneously. Out of these, it is preferred to carry out only the heat treatment or both of the heat treatment and the photoirradiation treatment.

EXAMPLES

The following examples are provided to further illustrate the present invention.

All the following operations were carried out in a dry nitrogen atmosphere unless stated otherwise. All the used solvents were dehydrated by means of Molecular Sieves 4A (of Union Showa K.K.) and deaerated by bubbling a nitrogen gas in advance.

The structures and mixing ratio of the synthesized complexes were checked by means of AVANCE 500 $^1$H-NMR of Bruker BioSpin K.K. at room temperature and a resolution of 500 MHz using deuterated benzene as a solvent.

In the following examples, required amounts in Examples were obtained by repeating the following Synthesis Examples on the following scales as required.

Synthesis Example 1

Synthesis of $AlH_3.N(C_2H_5)_3$ 3.80 g of lithium aluminum hydride was fed to a 200-ml three-necked flask containing a magnetic stir bar. A 100-ml dropping funnel for adding powders, a suction plug 3-way cock connected to a nitrogen gas stream and a glass stopper were connected to the three connection ports of the three-necked flask, respectively. 13.10 g of a hydrochloric acid salt of triethylamine was fed to the dropping funnel for adding powders, and then the three-necked flask was sealed up in nitrogen through the suction plug three-way cock.

100 ml of diethyl ether was added to the above three-necked flask by means of a glass syringe, and the whole vessel was kept at 0° C. in an iced bath. After the hydrochloric acid salt of triethylamine was gradually dropped into the three-necked flask over 10 minutes under agitation at 1,000 rpm with the magnetic stirrer, it was kept at 0° C. and further stirred for another 2 hours.

After the temperature of the whole vessel was returned to room temperature, the reaction mixture was pressure fed and collected into another vessel by using a polytetrafluoroethylene tube plugged up with absorbent cotton (absorbent cotton of Japanese Pharmacopoeia) at the end and filtered with a polytetrafluoroethylene membrane filter (manufactured by Whatman Inc.) having an opening diameter of 0.1 μm. The filtrate was received by a 300-ml eggplant-type flask, a magnetic stir bar was put into the flask after filtration, and a suction plug three-way cock was attached to the flask.

This suction plug three-way cock was connected to a vacuum pump through a trap to remove the solvent under reduced pressure while it was stirred at 300 rpm with the magnetic stirrer. After the removal of the solvent, the residue was filtered with a polytetrafluoroethylene membrane filter having an opening diameter of 0.1 μm (manufactured by Whatman Inc.) to obtain 5.90 g of an achromatic transparent liquid. When this achromatic transparent liquid was measured by $^1$H-NMR, it was confirmed that this was $AlH_3.N(C_2H_5)_3$ (yield of 45%).

Figure 1:
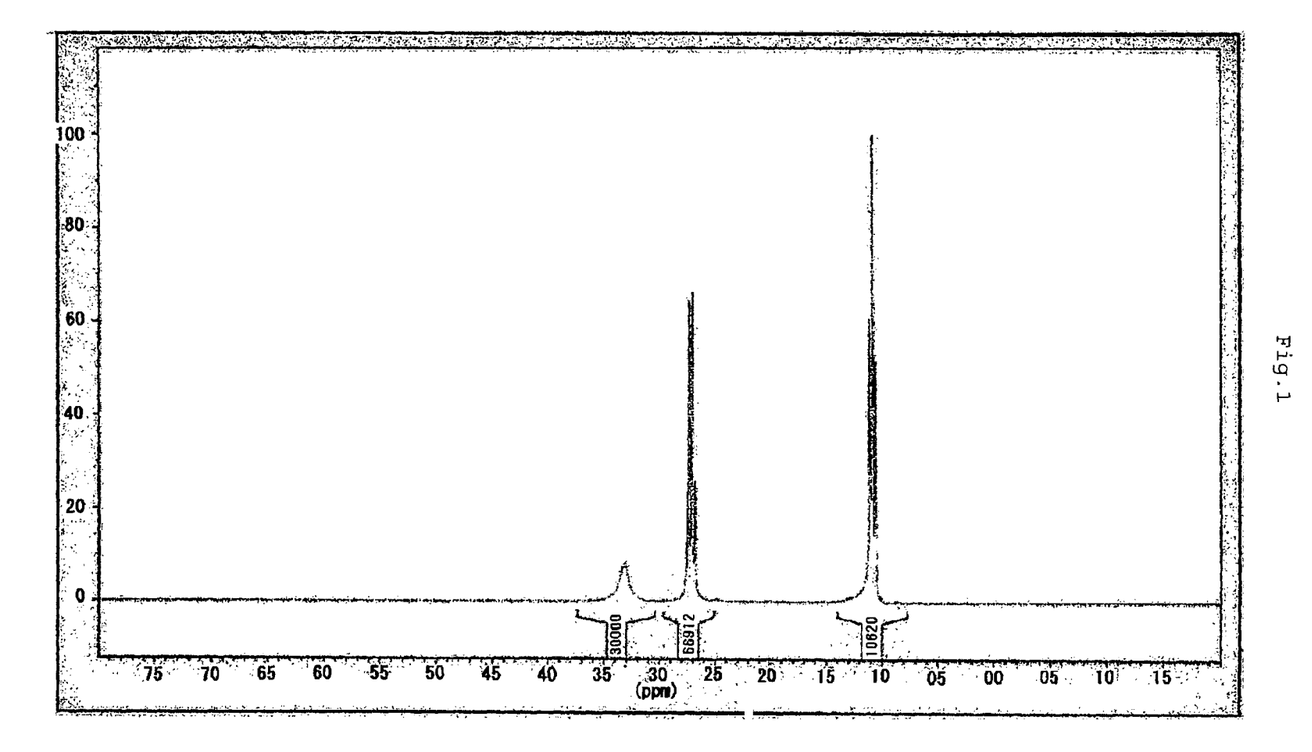
FIG. 1 is a $^1$H-NMR chart of $AlH_3 \cdot N(C_2H_5)_3$ synthesized in Synthesis Example 1.

The measured $^1$H-NMR chart is shown in FIG. 1.

<$^1$H-NMR Spectral Data>

1.06 ppm·1.08 ppm·1.10 ppm, 9H, tr (triplet)

2.65 ppm·2.70 ppm·2.77 ppm·2.82 ppm, 6H, dd (double doublet)

3.2 to 3.5 ppm, 3H, s (b) (singlet·broad)

Synthesis Example 2

Synthesis of $AlH_3.(N(C_2H_5)_3)_2$ 3.80 g of lithium aluminum hydride was fed to a 200-ml three-necked flask containing a magnetic stir bar. A 100-ml dropping funnel for adding powders, a suction plug 3-way cock connected to a nitrogen gas stream and a glass stopper were connected to the three connection ports of the three-necked flask, respectively. 28.80 g of a hydrochloric acid salt of triethylamine was fed to the dropping funnel for adding powders, and then the three-necked flask was sealed up in nitrogen through the suction plug three-way cock.

100 ml of hexane was added to the above three-necked flask by means of a glass syringe, and the temperature of the whole system was set to 35° C. After the hydrochloric acid salt of triethylamine was gradually dropped into the three-necked flask over 10 minutes under agitation at 1,000 rpm with the magnetic stirrer while this temperature was kept, it was kept at 35° C. and further stirred for another 2 hours.

After the temperature of the whole vessel was returned to room temperature, the reaction mixture was pressure fed and collected into another vessel by using a polytetrafluoroethylene tube plugged up with absorbent cotton (absorbent cotton of Japanese Pharmacopoeia) at the end and filtered with a polytetrafluoroethylene membrane filter having an opening diameter of 0.1 μm (manufactured by Whatman Inc.). The filtrate was received by a 300-ml eggplant-type flask, a magnetic stir bar was put into the flask after filtration, and a suction plug three-way cock was attached to the flask.

This suction plug three-way cock was connected to a vacuum pump through a trap to remove the solvent under reduced pressure while it was stirred at 300 rpm with the magnetic stirrer. After the removal of the solvent, the residue was distilled under a reduced pressure of 8 Pa by heating at 40° C. to collect a fraction having a temperature of 38° C. or higher. This fraction was filtered with a polytetrafluoroethylene membrane filter having an opening diameter of 0.1 μm (manufactured by Whatman Inc.) to obtain 4.17 g of an achromatic transparent liquid. When this achromatic transparent liquid was measured by $^1$H-NMR, it was confirmed that this was $AlH_3.(N(C_2H_5)_3)_2$ (yield of 18%).

Figure 2:
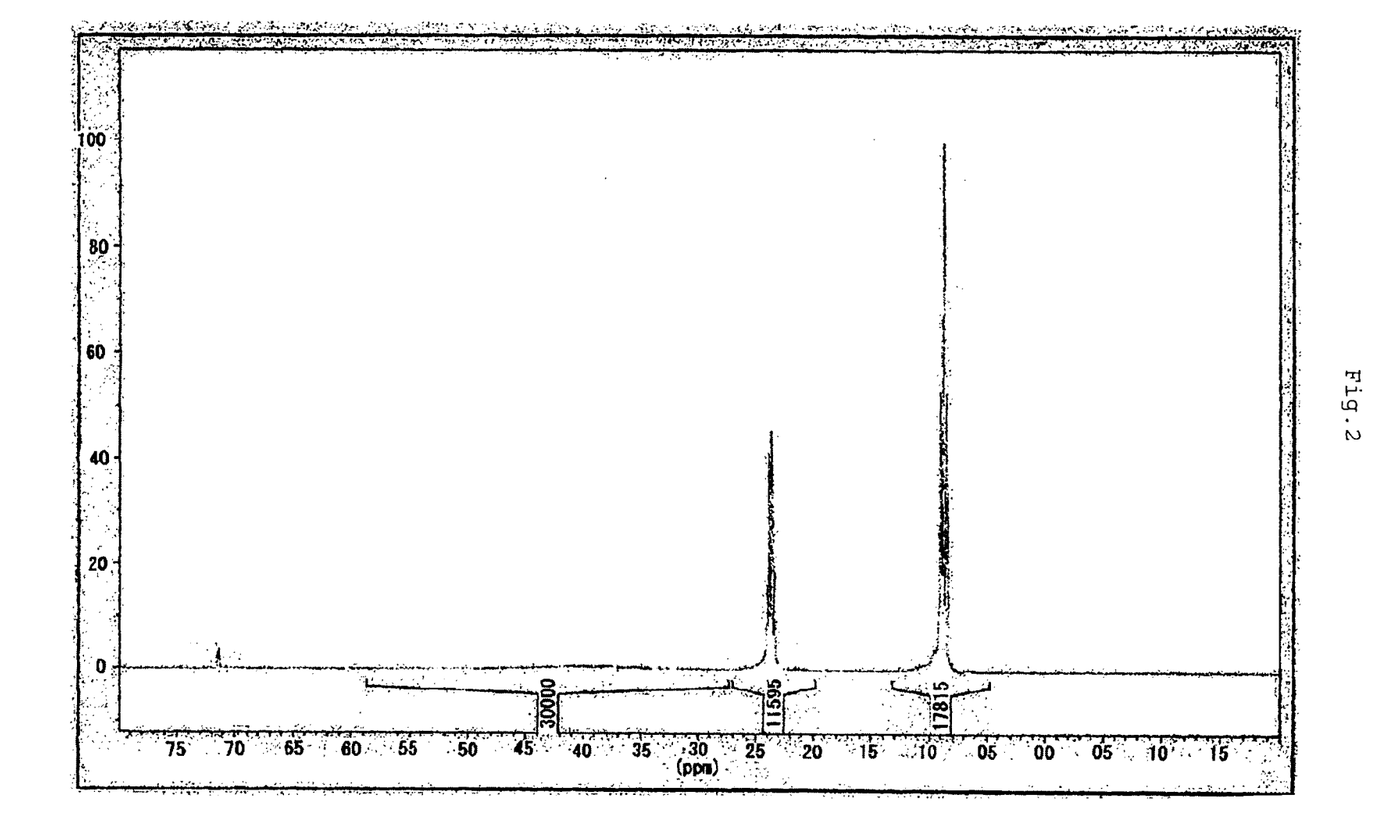
FIG. 2 is a $^1$H-NMR chart of $AlH_3 \cdot (N(C_2H_5)_3)_2$ synthesized in Synthesis Example 2.

The measured $^1$H-NMR chart is shown in FIG. 2.

<$^1$H-NMR Spectral Data>

0.86 ppm·0.88 ppm·0.90 ppm, 18H, tr (triplet)

2.34 ppm·2.36 ppm·2.39 ppm·2.41 ppm, 12H, dd (double doublet)

3.0 to 5.5 ppm, 3H, s (b) (singlet·broad)

Synthesis Example 3

Batch Synthesis (1) of a Mixture of $ALH_3. N(C_2H_5)_3$ and $AlH_3.(N(C_2H_5)_3)_2$)

3.80 g of lithium aluminum hydride was fed to a 200-ml three-necked flask containing a magnetic stir bar. A 100-ml dropping funnel for adding powders, a suction plug 3-way cock connected to a nitrogen gas stream and a glass stopper were connected to the three connection ports of the three-necked flask, respectively. 17.80 g of a hydrochloric acid salt of triethylamine was fed to the dropping funnel for adding powders, and then the three-necked flask was sealed up in nitrogen through the suction plug three-way cock.

100 ml of diethyl ether was added to the above three-necked flask by means of a glass syringe, and the temperature of the whole system was set to 10° C. After the hydrochloric acid salt of triethylamine was gradually dropped into the three-necked flask over 10 minutes under agitation at 1,000 rpm with the magnetic stirrer while this temperature was kept, it was further stirred at 10° C. for another 2 hours.

After the temperature of the whole vessel was returned to room temperature, the reaction mixture was pressure fed and collected into another vessel by using a polytetrafluoroethylene tube plugged up with absorbent cotton (absorbent cotton of Japanese Pharmacopoeia) at the end and filtered with a polytetrafluoroethylene membrane filter having an opening diameter of 0.1 μm (manufactured by Whatman Inc.). The filtrate was received by a 300-ml eggplant-like flask, a magnetic stir bar was put into the flask after filtration, and a suction plug three-way cock was attached to the flask.

This suction plug three-way cock was connected to a vacuum pump through a trap to remove the solvent under reduced pressure while it was stirred at 300 rpm with the magnetic stirrer. After the removal of the solvent, the residue was filtered with a polytetrafluoroethylene membrane filter having an opening diameter of 0.1 μm (manufactured by Whatman Inc.) to obtain 8.75 g of an achromatic transparent liquid. When this achromatic transparent liquid was measured by $^1$H-NMR, it was confirmed that this liquid was a mixture of $AlH_3.N(C_2H_5)_3$ and $AlH_3.(N(C_2H_5)_3)_2$ (mixing ratio of 80:20 (molar ratio)) (yield of 66%).

Figure 3:
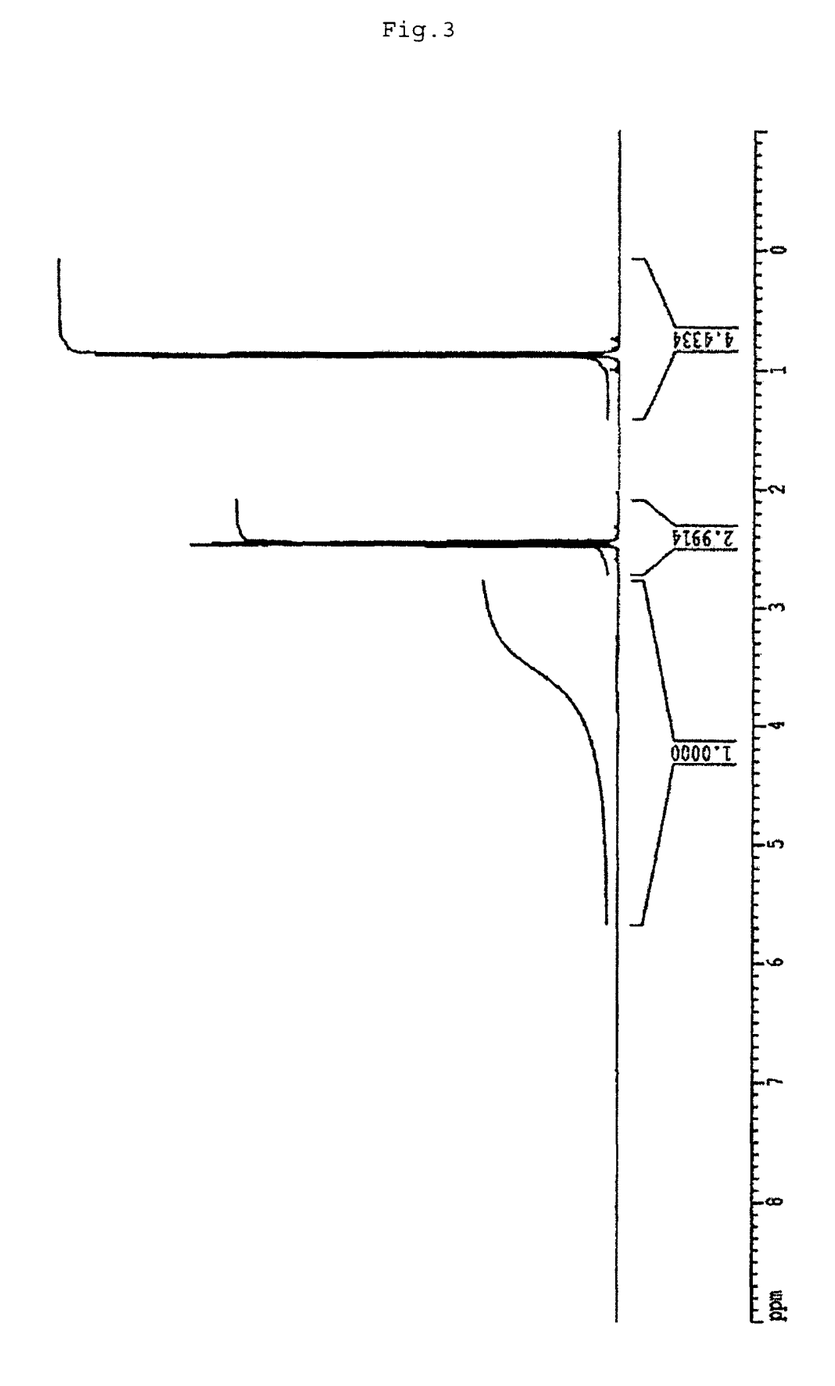
FIG. 3 is a $^1$H-NMR chart of a mixture of $AlH_3 \cdot (N(C_2H_5)_3$ and $AlH_3 \cdot (N(C_2H_5)_3)_2$ synthesized in Synthesis Example 3.

The measured $^1$H-NMR chart is shown in FIG. 3.

<$^1$H-NMR Spectral Data>

1.24 ppm·1.29 ppm·1.34 ppm, 10.8H, tr (triplet)

2.84 ppm·2.87 ppm·2.91 ppm·2.94 ppm, 7.2H, dd (double doublet)

3.3 to 3.9 ppm, 3H, s (b) (singlet broad)

Preparation Example 1

Preparation of a Solution Containing a Titanium Compound 0.11 g of cyclopentadienyltitanium trichloride was fed to a 30-ml glass vessel and 4-methylanisole was added to this to make the total amount 25.00 g. After the resulting mixture was fully stirred, it was left at room temperature for 4 hours and filtered with a polytetrafluoroethylene membrane filter having an opening diameter of 0.1 μm (manufactured by Whatman Inc.) to obtain a solution containing 20 μmol/g of cyclopentadienyltitanium trichloride.

Preparation Example 2

Preparation of a Composition for Forming a Base Film 0.30 g of bis(penta-2,4-diketo)titanium (IV) diisopropoxide and 64 μl of tetrakis(dimethylamino)titanium were fed to a 20-ml glass vessel, and 2-acetoxy-1-methoxypropane was added to the resulting mixture to make the total amount 18.00 g. After the mixture was fully stirred, it was left at room temperature for 2 hours. The mixture was filtered with a polytetrafluoroethylene membrane filter having an opening diameter of 0.1 μm (manufactured by Whatman Inc.) to obtain a composition for forming a base film.

Comparative Example 1

Preparation of a Composition for Forming an Aluminum Film 4-methylanisole was added to 8.00 g of $AlH_3.N(C_2H_5)_3$ obtained in the above Synthesis Example 1 to obtain the total amount of 16.00 g of a solution containing 50 wt % of $AlH_3.N(C_2H_5)_3$.

15 ml of the above solution was collected, and 0.81 ml of the solution containing 20 μmol/g of cyclopentadienyltitanium trichloride prepared in the above Preparation Example 1 was added to this under agitation at room temperature and further stirred for another 1 minute to prepare a composition for forming an aluminum film.

<Formation and Evaluation of Aluminum Film>

A silicon substrate was set on a spin coater, 1 ml of the composition for forming a base film prepared in the above Preparation Example 2 was dropped on the silicon substrate, and the silicon substrate was spun at 3,000 rpm for 10 seconds. This substrate was placed on a hot plate set at 150° C. and heated for 25 minutes to form a base film on the silicon substrate.

Then, this substrate having the base film was set on the spin coater again, 4 ml of the composition for forming an aluminum film prepared above was dropped on the substrate, and the substrate was spun at 800 rpm for 10 seconds. This substrate was heated on a 140° C. hot plate for 10 minutes. Thereafter, when it was further heated at 250° C. for 30 minutes, the surface of the substrate was covered with a film having metallic luster. When the ESCA spectrum of this film was observed, a peak attributed at $Al_{2p}$ was seen at 73.5 eV, whereby it was found that this film was an aluminum film.

The film thickness and density of this film were measured by the X'Pert MRD incident X-ray analyzer of Royal Phillips Electronics N.V., the reflectance for light having a wavelength of 540 nm of this film was measured by the U-4100 spectrophotometer of Hitachi High Technologies Corporation, and the specific resistance of the film was measured by the RT-80/RG-80 probe resistivity meter of Napson Corporation. The measurement results are shown in Table 1.

<Evaluation of Storage Stability>

About 5 ml of the composition for forming an aluminum film prepared above was fed to each of two glass vial containers having a capacity of 10 ml. These vial containers were kept at room temperature in a nitrogen atmosphere. The appearance of one of the vial containers was checked after 30 days, the appearance of the other vial container was checked after 60 days, and an attempt was made to form an aluminum film on a substrate in the same manner as above. After 30 days, a film could be formed and was evaluated. The results are shown in Table 3. It was confirmed from the ESCA spectrum that the formed film was an aluminum film. However, after 60 days, the content of the vial container formed a black precipitate, and a film could not be formed.

Example 1

Preparation of Composition for Forming an Aluminum Film 6.50 g (49.6 mmol) of $AlH_3.N(C_2H_5)_3$ synthesized in the above Synthesis Example 1 and 2.88 g (12.4 mmol) of $AlH_3.(N(C_2H_5)_3)_2$ synthesized in the above Synthesis Example 2 were fed to a 100-ml flask and stirred at a revolution of 1,000 rpm with a magnetic stirrer for 5 minutes to be fully mixed together.

8.00 g of the obtained complex mixture was collected, and 4-methylanisole was added to this to obtain the total amount of 16.00 g of a solution containing 50 wt % of a mixture of $AlH_3.N(C_2H_5)_3$ and $AlH_3.(N(C_2H_5)_3)_2$ (mixing ratio of 80:20 (molar ratio)).

15 ml of the above solution was collected, and 0.81 ml of the solution containing 20 µmol/g of cyclopentadienyltitanium trichloride prepared in the above Preparation Example 1 was added to this under agitation at room temperature and further stirred for another 1 minute to prepare a composition for forming an aluminum film.

<Formation and Evaluation of Aluminum Film and Evaluation of Storage Stability>

An aluminum film was formed on a substrate and evaluated in the same manner as in Comparative Example 1 except that the composition for forming an aluminum film prepared above was used. The evaluation of storage stability was carried out as well. The evaluation results are shown in Tables 1 and 2.

It was confirmed from the ESCA spectrum that the formed films were all aluminum films.

Examples 2 to 5 and Comparative Examples 2 to 4

Compositions for forming an aluminum film were prepared in the same manner as in Example 1 except that the mixing ratio of $AlH_3.N(C_2H_5)_3$ and $AlH_3.(N(C_2H_5)_3)_2$ mixed together in the <preparation of composition for forming an aluminum film> in the above Example 1 was changed as shown in Table 1 and used to form an aluminum film on a substrate in the same manner as in Comparative Example 1 and evaluate it. The evaluation of storage stability was carried out as well. The evaluation results are shown in Tables 1 and 2.

It was confirmed from the ESCA spectra that the formed films were all aluminum films.

Comparative Example 5

A composition for forming an aluminum film was prepared in the same manner as in the above Comparative Example 1 except that $AlH_3.(N(C_2H_3)_2$ was used in place of $AlH_3.N(C_2H_5)_3$ in the <preparation of composition for forming an aluminum film> in the above Comparative Example 1 and used to form an aluminum film on a substrate in the same manner as in Comparative Example 1 and evaluate it. The evaluation of storage stability was carried out as well. The evaluation results are shown in Tables 1 and 2.

It was confirmed from the ESCA spectrum that the formed films were all aluminum films.

Example 6

A composition for forming an aluminum film was prepared in the same manner as in the above Comparative Example 1 except that the mixture of $AlH_3.N(C_2H_5)_3$ and $AlH_3.(N(C_2H_5)_3)_2$ (mixing ratio of 8:2 (molar ratio)) synthesized in a batch manner in the above Synthesis Example 3 was used in place of $AlH_3.N(C_2H_5)_3$ in the <preparation of composition for forming an aluminum film> in Comparative Example 1 and used to form an aluminum film on a substrate in the same manner as in Comparative Example 1 and evaluate it. The evaluation of storage stability was carried out as well. The evaluation results are shown in Tables 1 and 2.

It was confirmed from the ESCA spectrum that the formed films were all aluminum films.

TABLE 1

| | Aluminum complex | | | Aluminum film | | |
|---|---|---|---|---|---|---|
| | Amount of mono-adduct (g) | Amount of bis-adduct (g) | Molar ratio | Film thickness (nm) | Reflectance (%) | Specific resistance (µΩcm) |
| C. Ex. 1 | 8.00 | 0 | 100:0 | 140 | 83 | 3.8 |
| Ex. 1 | 6.50 | 2.88 | 80:20 | 140 | 83 | 3.8 |
| Ex. 2 | 5.69 | 4.32 | 70:30 | 141 | 83 | 3.8 |
| Ex. 3 | 4.87 | 5.75 | 60:40 | 142 | 82 | 3.8 |
| Ex. 4 | 4.01 | 7.19 | 50:50 | 140 | 80 | 3.8 |
| Ex. 5 | 3.25 | 8.63 | 40:60 | 146 | 80 | 3.9 |
| C. Ex. 2 | 2.44 | 10.07 | 30:70 | 145 | 78 | 4.4 |
| C. Ex. 3 | 1.62 | 11.51 | 20:80 | 150 | 70 | 4.7 |
| C. Ex. 4 | 0.81 | 12.95 | 10:90 | 148 | 71 | 4.6 |
| C. Ex. 5 | 0 | 8.00 | 0:100 | 152 | 68 | 4.7 |
| Ex. 6 | Batch synthesis | | 80:20 | 143 | 83 | 3.8 |

Ex.: Example
C. Ex.: Comparative Example

TABLE 2

| | Molar ratio of aluminum complexes | Storage stability | | | | | |
|---|---|---|---|---|---|---|---|
| | | After 30 days | | | After 60 days | | |
| | | Film thickness (nm) | Reflectance (%) | Specific resistance (μΩcm) | Film thickness (nm) | Reflectance (%) | Specific resistance (μΩcm) |
| C. Ex. 1 | 100:0 | 155 | 78 | 4.5 | Black precipitate was formed and film formation was impossible | | |
| Ex. 1 | 80:20 | 140 | 83 | 3.8 | 141 | 82 | 3.9 |
| Ex. 2 | 70:30 | 140 | 82 | 3.9 | 140 | 81 | 3.8 |
| Ex. 3 | 60:40 | 145 | 80 | 4.0 | 149 | 80 | 4.2 |
| Ex. 4 | 50:50 | 146 | 80 | 3.8 | 151 | 78 | 4.4 |
| Ex. 5 | 40:60 | 146 | 80 | 3.9 | 152 | 78 | 4.5 |
| C. Ex. 2 | 30:70 | 157 | 72 | 5.1 | 157 | 72 | 5.5 |
| C. Ex. 3 | 20:80 | 150 | 68 | 4.7 | 153 | 70 | 4.9 |
| C. Ex. 4 | 10:90 | 150 | 65 | 4.8 | 155 | 68 | 4.6 |
| C. Ex. 5 | 0:100 | 152 | 62 | 4.9 | 152 | 63 | 4.9 |
| Ex. 6 | 80:20 | 141 | 82 | 3.8 | 141 | 82 | 3.9 |

Ex.: Example
C. Ex.: Comparative Example

The symbols in the column of aluminum complex of Table 1 denote the following substances.
mono-adduct: $AlH_3 \cdot N(C_2H_5)_3$
bis-adduct: $AlH_3 \cdot (N(C_2H_5)_3)_2$

EFFECT OF THE INVENTION

According to the present invention, there are provided a composition for forming an aluminum film, having excellent long-term storage stability, which is industrially advantageous, and a simple method of forming an aluminum film by applying the composition. The method of forming an aluminum film of the present invention is easily applied to a large-sized substrate and contributes to cost reduction.

The invention claimed is:

1. A composition, comprising a complex represented by formula (1) and a complex represented by formula (2), $$AlH_3 \cdot NR^1R^2R^3 \quad (1)$$

$$AlH_3 \cdot (NR^1R^2R^3)_2 \quad (2),$$

wherein $R^1$, $R^2$ and $R^3$ are each independently a hydrogen atom, alkyl group, cycloalkyl group, alkenyl group, alkynyl group, aryl group or aralkyl group, and
wherein the molar ratio of the complex represented by the formula (1) and the complex represented by the formula (2) is 70:30 to 85:15.

2. The composition according to claim 1, wherein the molar ratio of the complex represented by the formula (1) and the complex represented by the formula (2) is 70:30 to 80:20.

3. The composition according to claim 2, further comprising a titanium compound.

4. The composition according to claim 1, further comprising a titanium compound.

5. A method of forming an aluminum film, comprising:
applying the composition according to claim 4 to a substrate to form a coating film; and
subjecting the coating film to at least one of a heat treatment and a photoirradiation treatment.

6. The method of forming an aluminum film according to claim 5, wherein the substrate has a base film thereon that comprises an organic metal compound comprising at least one metal selected from the group consisting of titanium, palladium and aluminum excluding the complex represented by formula (1) and the complex represented by formula (2), and wherein the composition is applied to the base film on the substrate.

7. A method of producing the composition according to claim 4, comprising:
synthesizing the complex represented by formula (1) by reacting lithium aluminum hydride with a hydrohalogenic acid salt of a compound represented by formula (3) in an ether solvent at a temperature of 0° C. or lower;
synthesizing the complex represented by formula (2) by reacting lithium aluminum hydride with a hydrohalogenic acid salt of a compound represented by formula (3) in a hydrocarbon solvent at a temperature higher than 30° C.; and
mixing the complexes together:

$$NR^1R^2R^3 \quad (3)$$

wherein, $R^1$, $R^2$ and $R^3$ are each independently a hydrogen atom, alkyl group, cycloalkyl group, alkenyl group, alkynyl group, aryl group or aralkyl group.

8. A method of forming an aluminum film, comprising:
applying the composition according to claim 1 to a substrate to form a coating film; and
subjecting the coating film to at least one of a heat treatment and a photoirradiation treatment.

9. The method of forming an aluminum film according to claim 8, wherein the substrate has a base film thereon that comprises an organic metal compound comprising at least one metal selected from the group consisting of titanium, palladium and aluminum excluding the complex represented by formula (1) and the complex represented by formula (2), and wherein the composition is applied to the base film on the substrate.

10. A method of producing the composition according to claim 1, comprising:
synthesizing the complex represented by formula (1) by reacting lithium aluminum hydride with a hydrohalogenic acid salt of a compound represented by formula (3) in an ether solvent at a temperature of 0° C. or lower;
synthesizing the complex represented by formula (2) by reacting lithium aluminum hydride with a hydrohalogenic acid salt of a compound represented by formula (3) in a hydrocarbon solvent at a temperature higher than 30° C.; and mixing the complexes together:

$$NR^1R^2R^3 \quad (3)$$

wherein, $R^1$, $R^2$ and $R^3$ are each independently a hydrogen atom, alkyl group, cycloalkyl group, alkenyl group, alkynyl group, aryl group or aralkyl group.

\* \* \* \* \*